United States Patent [19]

Mignani et al.

[11] Patent Number: 4,806,280
[45] Date of Patent: Feb. 21, 1989

[54] PROCESS FOR THE PREPARATION OF UNSATURATED COMPOUND α-CHLORINATED WITH RESPECT TO TWO ELECTRON-ATTRACTING GROUPS IN A β-POSITION

[75] Inventors: Gerard Mignani, Lyon; Didier Morel, Villiers sur Orge, both of France

[73] Assignee: Rhone-Poulenc Sante, Courbevoie, France

[21] Appl. No.: 81,634

[22] Filed: Aug. 3, 1987

Related U.S. Application Data

[63] Continuation of Ser. No. 753,530, Jul. 10, 1985, abandoned.

[30] Foreign Application Priority Data

Jul. 12, 1984 [FR] France .................. 84 11088

[51] Int. Cl.$^4$ .................. C07C 69/60; C11C 3/00
[52] U.S. Cl. .................. 260/408; 558/460; 560/174; 564/204; 564/209; 568/407; 568/495; 568/946
[58] Field of Search .................. 560/174; 564/204, 209; 558/460; 568/407, 495, 946; 260/408

[56] References Cited

U.S. PATENT DOCUMENTS 2,481,036  9/1949  Price et al. .................. 260/408
2,788,360  4/1957  Westfahl .................. 549/74
3,277,147  10/1966  Machleidt .................. 560/125

FOREIGN PATENT DOCUMENTS 0082781  6/1983  European Pat. Off. .................. 560/174

OTHER PUBLICATIONS

Isler, Otto, *La Chimica E L'Industria*, vol. 49 (1967), pp. 1317–1332.
*Beilsteins Handbuch der Organischen Chemie*, 4th Ed., vol. 1 1 (1918), at p. 78.
*Berichte der Deutschen Chemischen Gesellschaft*, vol. 13 (1880), at p. 600.
Krauch, Helmut et al., *Organic Reactions*, (1964), John Wiley & Sons, Publ., pp. 1, 2 and 302.
P. L. Slotter, Tetrahedron Letters No. 40, 4067–4070 1972).
P. Karrer et al., Chem. Abstr. 46, 2550 e (1952).
Kosower et al., Organic Chemistry, 28, 630–633 (1963)
* This Reference was Cited by the Examiner in Ser. No. 450,267.
Kosicki et al., Chem. Abstr., 62, 5184 b (1965).

Warnhoff et al., Organic Syntheses, Coll., vol. IV, 162–166 (1963).
Krapcho et al., J. Org. Chem., 43, 138–147 (1978).

*Primary Examiner*—Paul J. Killos
*Attorney, Agent, or Firm*—Stevens, Davis, Miller & Mosher

[57] ABSTRACT

Compounds of formula

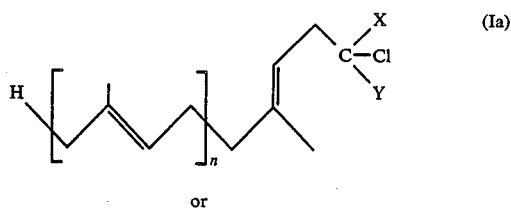

or

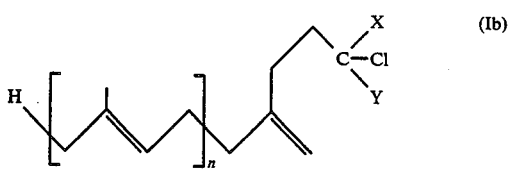

in which n denotes an integer from 1 to 10 and X and Y, which are identical or different, each denote an electron-attracting group, are made by reacting a halogenating agent with a compound of formula

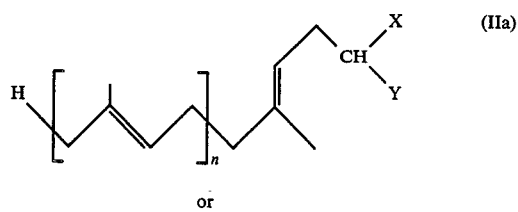

or

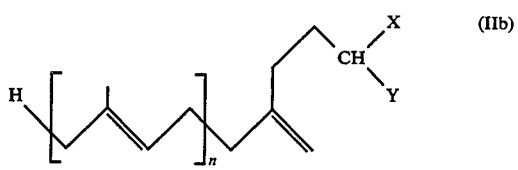

in which R, X and Y are as hereinbefore defined, anionized by a base.

6 Claims, No Drawings

PROCESS FOR THE PREPARATION OF UNSATURATED COMPOUND α-CHLORINATED WITH RESPECT TO TWO ELECTRON-ATTRACTING GROUPS IN A β-POSITION

This application is a continuation of application Ser. No. 753,530, filed on July 10, 1985, now abandoned.

The present invention provides a process for the preparation of unsaturated compounds α-chlorinated with respect to two electron-attracting groups in a β-position, of formula

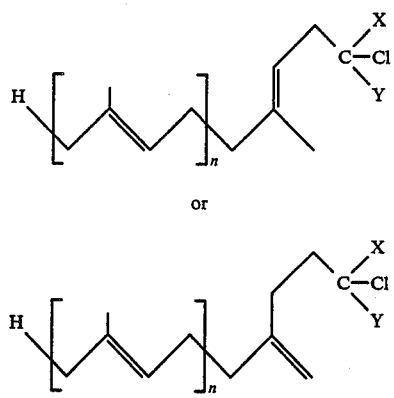

in which n denotes an integer from 1 to 10 and X and Y, which are identical or different, each denote an electron-attracting group chosen from —CHO, —COR$_1$, —COOR$_2$, —CONR$_3$R$_4$, —CN, —SO$_2$R$_5$ and NO$_2$, in which R$_1$, R$_2$, R$_3$, R$_4$ and R$_5$ each denote an alkyl radical of 1 to 4 carbon atoms, and R$_5$ may also denote a phenyl radical which is unsubstituted or substituted by methyl.

The compounds of general formula Ia and Ib in which one of the symbols X and Y denotes —COR$_1$ and the other denotes —COOR$_2$ are of particular interest.

European Patent Application EP No. 00 82 781 denotes a process for the preparation of α-chloro-β-keto esters by the reaction of cupric chloride, in the presence of lithium chloride, in a basic polar aprotic solvent, such as N-methylpyrrolidone, at a temperature of between 15° and 50° C., with the corresponding β-keto ester.

According to P. L. Stotter and K. A. Hill, Tetrahedron Letters, No. 40, 4067 (1972), it is known to prepare α-bromo-β-keto esters from the corresponding β-keto esters by reaction with sodium hydride followed by a fast reaction with bromine in methylene chloride at 0° C.

However, it is known, particularly according to M. L. Poutsma, J. Amer. Chem. Soc., 87, (19), 4285 (1965), that the chlorination of ethylenic compounds with chlorine in the presence of oxygen at ambient temperature results substantially in addition products together with products of allylic substitution.

According to U.S. Pat. No. 2,995,600, the chlorination of myrcene with gaseous chlorine results in the formation of 3-chloro-2-methyl-6-methylene-1,7-octadiene.

It is also known, from U.S. Pat. No. 4,272,412, that the chlorination of dihydro-α-ionone with a hypohalous acid prepared in situ results in 4-(5-chloro-6-methylene-2,2-dimethylcyclohexyl)-2-butanone without the formation of a product α-chlorinated with respect to the ketone group.

Furthermore, when a halogenating agent such as molecular chlorine or sulphuryl chloride in a polar aprotic solvent is reacted with a compound of formula (IIa) or (IIb), in which n, X and Y are defined as previously, only products of halogenation of the terpene chain are formed, without the formation of a compound α-chlorinated with respect to the X and Y groups being observed.

It has now been found, and this is the subject of the present invention, that the compounds of formula (Ia) or (Ib) can be obtained by the reaction of a halogenating agent capable of providing a Cl+ cation with a compound of formula

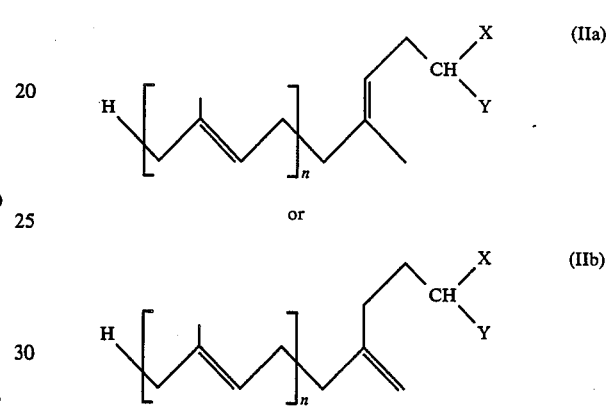

in which n, X and Y are as hereinbefore described, anionized with a base.

In the process of the invention it is particularly advantageous to add the anionizing agent and the halogenating agent to the compound of general formula (IIa) or (IIb) in solution in a suitable anhydrous organic solvent.

It is also possible first to anionize the compound of formula (IIa) or (IIb) and then subsequently to add the halogenating agent.

Anionizing agents which are particularly suitable include hydrides, amides, hydroxides and carbonates of an alkali or alkaline-earth metal (e.g. sodium, potassium, or calcium), and non-quaternizable amines (e.g. 1,8-diazabicyclo[5.4.0]undec-7-ene (DBU), collidines, ethyldiisopropylamine, or ethyldicyclohexylamine).

The organic solvent may be an aliphatic hydrocarbon (e.g. pentane or hexane), an aromatic hydrocarbon (e.g. benzene or toluene), an ether (e.g. ethyl ether, methyl tert-butyl ether, or tetrahydrofuran), a ketone (e.g. acetone, or methyl isobutyl ketone), a tertiary amide (e.g. dimethylformamide, or N-methylpyrrolidone), a nitrile (e.g. acetonitrile), a nitrated solvent (e.g. nitrobenzene, or nitromethane) or, when the operation is carried out in the presence of a phase transfer catalyst such as tetrabutylammonium hydrogen sulphate, a polychlorinated solvent (e.g. methylene chloride).

The halogenating agent is a source of Cl+ cations, and is preferably molecular chlorine, sulphuryl chloride, N-chlorosuccinimide or hexachloroethane.

The process is generally carried out at a temperature of between 0° and 120° C. and, preferably, in the region of 25° C.

The process according to the invention can also be carried out using an alkali metal alcoholate (e.g. sodium methylate) as an anionizing agent in the corresponding alcohol (e.g methanol). However, under these conditions, the anionization and the halogenation should preferably be carried out at a temperature below 0° C. and usually at below −30° C. and more particularly at a temperature in the region of −50° C.

A stoichiometric quantity of the anionizing agent and of the halogenating agent relative to the compound of formula (IIa) or (IIb) employed is generally used.

The products of general formula (Ia) or (Ib) which are obtained by the process of the present invention may be isolated from the reaction medium by the usual extraction methods and may be purified by applying physical-chemical methods such as distillation or chromatography.

The compounds of formula (IIa) or (IIb) can be obtained by selective addition of a compound containing an active methylene group, of formula

(III)

in which X and Y are defined as previously, with a butadiene of formula

(IV)

in which n is defined as previously, under the conditions described in European Patent No. 00 44 771.

The compounds of formula (Ia) and (Ib) are of particular interest as intermediates in organic chemistry. For example, the compounds of formula (Ia) and (Ib), in which one of X and Y denotes —COCH$_3$ and the other —COOR$_2$ can be used to make ethylenic ketones of formula

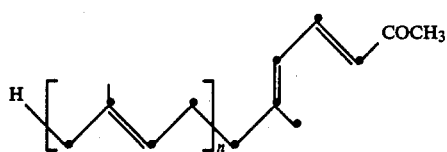

(V)

in which n is defined as previously, in the form of a mixture of the EE or EZ isomers.

Compounds of formula (V) may more particularly be made by decarboxylating the compound of formula (Ia) or (Ib) in which one of the symbols X or Y denotes a radical —COCH$_3$ and the other a radical —COOR$_2$ to produce an α-haloketone of formula

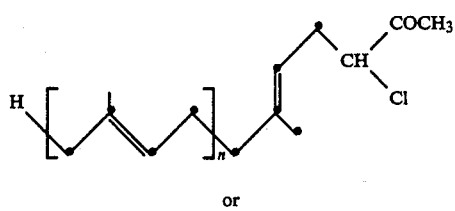

(VIa)

or

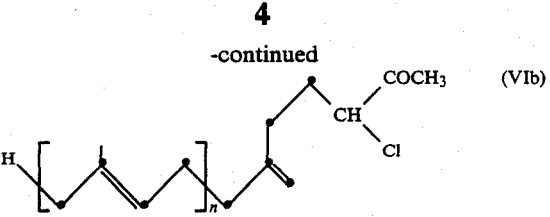

(VIb)

in which n is defined as previously, which is then dehydrohalogenated to produce the product of formula (V).

The decarboxylation and dehydrohalogenation reactions may be carried out without isolation of the α-haloketone of general formula (VIa) or (VIb).

The successive or simultaneous decarboxylation and dehydrohalogenation reactions may be carried out under the conditions described in European Patent Application EP No. 00 82 781. For example, the compound of general formula (V), in which n=1, is pseudionone, which may be converted to vitamin A using known methods.

The following Examples illustrate the invention.

EXAMPLE 1

A mixture of:
(CH$_3$)$_2$C=CH—CH$_2$CH$_2$—C(=CH$_2$)—CH$_2$—CH$_2$—CH(COOCH$_3$)COCH$_3$ and
(CH$_3$)$_2$C=CH—CH$_2$CH$_2$—C(CH$_3$)=CH—CH$_2$—CH(COOCH$_3$)COCH$_3$
(2.52 g; 0.01 mole) is introduced, under an argon atmosphere into a 100 cc round bottomed flask and ground potassium hydroxide (0.6 g; 0.0107 mole) and hexachloroethane (2.5 g; 0.0105 mole) are then added. The mixture is stirred at 25° C. for 12 hours. The reaction mixture is poured into water (100 cc) and then extracted with ethyl ether (3×30 cc). The organic phases are combined and dried over magnesium sulphate. After filtration and evaporation of the solvent a slightly yellow oil (3.75 g) is obtained. Distillation under reduced pressure (0.1 mm Hg; 0.013 kPa) at 150° C. produces a 55/45 mixture of:
(CH$_3$)$_2$C=CH—CH$_2$CH$_2$—C(=CH$_2$)CH$_2$CH$_2$—CCl(COOCH$_3$)COCH$_3$ and
(CH$_3$)$_2$C=CH—CH$_2$CH$_2$—C(CH$_3$)=CH—CH$_2$—CCl(COOCH$_3$)COCH$_3$
(2.5 g), which assays at 81%.

The yield of isolated products is 70%.

EXAMPLE 2

N-Methylpyrrolidone (50 cc) and a 55/45 mixture of:
(CH$_3$)$_2$C=CH—CH$_2$CH$_2$—C(=CH$_2$)—CH$_2$CH$_2$—CH(COOCH$_3$)COCH$_3$ and
(CH$_3$)$_2$C=CH—CH$_2$CH$_2$—C(CH$_3$)=CH—CH$_2$—CH(COOCH$_3$)COCH$_3$
(5.5 g; 0.0218 mole) are introduced, under an argon atmosphere, into a 100 cc round flask and then sodium carbonate (2.49 g; 0.0235 mole) and hexachloroethane (5.24 g; 0.0221 mole) are added. The mixture is stirred at 25° C. for 20 hours. A white precipitate is seen to form. After filtration, the reaction mixture is poured into water (150 cc) and is then extracted with ethyl ether (3×50 cc). The organic phases are combined and dried over sodium sulphate. After filtration and evaporation of the solvent a slightly yellow oil (7.47 g) consisting of a 55/45 mixture of:
(CH$_3$)$_2$C=CH—CH$_2$CH$_2$—C(=CH$_2$)—CH$_2$—CH$_2$—CCl(COOCH$_3$)COCH$_3$ and $(CH_3)_2C=CH-CH_2CH_2-C(CH_3)=CHCH_2-CCl(COOCH_3)COCH_3$.

is obtained.

Analysis by gas phase chromatography with an internal standard shows that:
the conversion is 98%
the yield is 97%.

EXAMPLE 3

N-Methylpyrrolidone (50 cc) and a 55/45 mixture of:
$(CH_3)_2C=CH-CH_2CH_2-C(=CH_2)-CH_2CH_2-CH(COOCH_3)COCH_3$ and
$(CH_3)_2C=CH-CH_2CH_2-C(CH_3)=CH-CH_2-CH(COOCH_3)COCH_3$
(4.8 g; 0.0190 mole) are introduced, under an argon atmosphere, into a 100 cc round flask and then ground potassium hydroxide (1.10 g; 0.01964 mole) and hexachloroethane (5 g; 0.021 mole) are added. The mixture is stirred at 25° C. for 40 minutes. The reaction mixture is poured into water (100 cc) and then extracted with ethyl ether (3×50 cc). The organic phases are combined and dried over sodium sulphate. After filtration and evaporation of the solvent a slightly yellow oil (8.2 g) is obtained, which contains a 55/45 mixture of:
$(CH_3)_2C=CH-CH_2CH_2-C(=CH_2)CH_2CH_2-CCl(COOCH_3)COCH_3$ and
$(CH_3)_2C=CH-CH_2CH_2-C(CH_3)=CH-CH_2-CCl(COOCH_3)COCH_3$
Analysis by gas phase chromatography with an internal standard shows that:
the conversion is in the region of 98–99%
the yield is 90%.

EXAMPLE 4

Hexane (15 cc), N-methylpyrrolidone (5 cc), potassium hydroxide (0.56 g; 0.01 mole) and then a 55/45 mixture of:
$(CH_3)_2C=CH-CH_2CH_2-C(=CH_2)CH_2CH_2-CH(COOCH_3)COCH_3$ and
$(CH_3)_2C=CH-CH_2CH_2-C(CH_3)=CH-CH_2CH-(COOCH_3)COCH_3$.
(2.52 g; 0.01 mole) are introduced, under an argon atmosphere, into a 100 cc round flask. Hexachloroethane (2.36 g; 0.01 mole) is then added. The mixture is stirred at 25° C. for 15 hours. The reaction mixture is poured into water (100 cc) and then extracted with ethyl ether (3×50 cc). The combined organic phases are dried over magnesium sulphate. After filtration and evaporation of the solvent a slightly yellow oil (3.9 g) consisting of a 55/45 mixture of:
$(CH_3)_2C=CH-CH_2CH_2-C(=CH_2)-CH_2CH_2-CCl(COOCH_3)COCH_3$ and
$(CH_3)_2C=CH-CH_2CH_2-C(CH_3)=CH-CH_2-CCl(COOCH_3)COCH_3$.
is obtained.

The yield of isolated product after a flash-distillation is 70%.

EXAMPLE 5

N-Methylpyrrolidone (20 cc) and a 55/45 mixture of:
$(CH_3)_2C=CH-CH_2CH_2-C(=CH_2)CH_2CH_2-CH(COOCH_3)COCH_3$ and
$(CH_3)_2C=CH-CH_2CH_2-C(CH_3)=Ch-CH_2-CH(COOCH_3)COCH_3$,
(2.52 g; 0.01 mole) are introduced, under an argon atmosphere, into a 100 cc round flask and then potassium carbonate (1.5 g; 0.0108 mole) and hexachloroethane (2.36 g; 0.01 mole) are added. The mixture is stirred at 25° C. for 24 hours. The reaction mixture is poured into water (100 cc) and then extracted with ethyl ether (3×50 cc). The combined organic phases are dried over magnesium sulphate. After filtration and evaporation of the solvent a slightly yellow oil (3 g) consisting of a 55/45 mixture of:
$(CH_3)_2C=CH-CH_2CH_2-C(=CH_2)-CH-CH_2-CCl(COOCH_3)COCH_3$ and
$(CH_3)_2C=CH-CH_2CH_2-C(CH_3)=CH-CH_2-CCl(COOCH_3(COCH_3$
is obtained.

The conversion is 80%.
The yield of isolated product is 73%.

EXAMPLE 6

Tetrahydrofuran (20 cc) and a 55/45 mixture of:
$(CH_3)_2C=CH-CH_2CH_2-C(=CH_2)CH_2CH_2-CH(COOCH_3)COCH_3$ and
$(CH_3)_2C=CH-CH_2CH_2-C(CH_3)=CH-CH_2-CH(COOCH_3)COCH_3$
(2.52 g; 0.01 mole) are introduced, under an argon atmosphere, into a 100 cc round flask and then potassium hydroxide (0.56 g; 0.01 mole) and hexachloroethane (2.5 g; 0.0105 mole) are added. The mixture is stirred at 25° C. for 10 hours. The reaction mixture is poured into water (100 cc) and extracted with ethyl ether (3×50 cc). The combined organic phases are dried over magnesium sulphate. After filtration and evaporation of the solvent a slightly yellow oil consisting of a 55/45 mixture of:
$(CH_3)_2C=CH-CH_2CH_2-C(=CH_2)-CH_2CH_2-CCl(COOCH_3)COCH_3$ and
$(CH_3)_2C=CH-CH_2CH_2-C(CH_3)=CH-CH_2-CCl(COOCH_3)COCH_3$
is obtained.

The yield of isolated product is 70%.

EXAMPLE 7

Methanol (20 cc) and, in small portions, sodium (0.23 g; 0.01 gramme-atom) are introduced, under an argon atmosphere, into a 100 cc round flask. The mixture is cooled to −50° C. and then a 55/45 mixture of:
$(CH_3)_2C=CH-CH_2CH_2-C(=CH_2)CH_2CH_2-CH(COOCH_3)COCH_3$ and
$(CH_3)_2C=CH-CH_2CH_2-C(CH_3)=CH-Ch_2-CH(COOCH_3)COCH_3$.
(2.52 g; 0.01 mole) and N-chlorosuccinimide (1.33 g; 0.01 mole) are added. The mixture is stirred at −50° C. for 40 minutes. After evaporation of the methanol the reaction mixture is poured into water (100 cc) and then extracted with ethyl ether (3×50 cc). The combined organic phases are dried over magnesium sulphate. After filtration and evaporation of the solvent and after a flash-distillation a slightly yellow oil (2.5 g) is obtained, consisting of a 55/45 mixture of:
$(CH_3)_2C=CH-CH_2CH_2-C(=CH_2)CH_2CH_2-CCl(COOCH_3)COCH_3$ and
$(CH_3)_2C=CH-CH_2CH_2-C(CH_3)=CH-CH_2-CCl(COOCH_3)COCH_3$.
The yield is 87%.

EXAMPLE 8

Hexane (500 cc) and sodamide (4.04 g; 0.103 mole) are introduced, under an argon atmosphere, into a 1,200 cc reactor. The mixture is cooled to 5° C. and then a solution of a 55/45 mixture of:

(CH₃)₂C=CH—CH₂CH₂—C(=CH₂)CH₂CH₂—CH-(COOCH₃)COCH₃ and
(CH₃)₂C=CH—CH₂CH₂—C(CH₃)=CH—CH₂—CH-(COOCH₃)COCH₃

(24.4 g; 0.097 mole) in hexane (100 cc) is added slowly over 1 hour and 40 minutes. The mixture is then stirred at 5° C. for 5 hours; 95% of the theoretical quanity of ammonia is evolved. A solution of sulphuryl chloride (14.5 g; 0.107 mole) in hexane (50 cc) is then added over 45 minutes. The mixture is stirred for 1 hour and 30 minutes; a white precipitate is seen to form. After filtration and evaporation of the solvent a slightly yellow oil (31.2 g) consisting of a 55/45 mixture of:
(CH₃)₂C=CH—CH₂CH₂—C(=CH₂)CH₂CH₂—CCl-(COOCH₃)COCH₃ and
(CH₃)₂C=CH—CH₂CH₂—C(CH₃)=CH—CH₂—CCl(COOCH₃)COCH₃
is obtained.

A determination by gas phase chromatography with an internal standard shows that:
the conversion is 93.5%
the yield is 90.2%.

EXAMPLE 9

Toluene (80 cc) and sodamide (0.76 g; 0.0194 mole) are introduced, under an argon atmosphere, into a 250 cc reactor. The mixture is cooled to a temperature of between 5° and 10° C. and then a solution of a 55/45 mixture of:
(CH₃)₂C=CH—CH₂CH₂—C(=CH₂)CH₂CH₂—CH-(COOCH₃)COCH₃ and
(CH₃)₂C=CH—CH₂CH₂—C(CH₃)=CH—CH₂—CH-(COOCH₃)COCH₃

(4.96 g; 0.0197 mole) in toluene (20 cc) is added. The mixture is allowed to react at 25° C. for 2 hours and then a solution of sulphuryl chloride (2.89 g; 0.0215 mole) in toluene (10 cc) is added. The mixture is stirred for 1 hour. After filtration and evaporation of the solvent a slightly yellow oil (5.63 g) is obtained, consisting of a 55/45 mixture of:
(CH₃)₂C=CH—CH₂CH₂—C(=CH₂)—CH₂CH₂—CCl(COOCH₃)COCH₃ and
(CH₃)₂C=CH—CH₂CH₂—C(CH₃)=CH—CH₂—CCl(COOCH₃)COCH₃

Analysis by gas phase chromatography with an internal standard shows that the yield is 66.8%.

EXAMPLE 10

Methanol (20 cc) and, in small portions, sodium (0.23 g; 0.01 gramme-atom) are introduced, under an argon atmosphere, into a 100 cc round flask. The mixture is cooled to −50° C. and then a 55/45 mixture of:
(CH₃)₂C=CH—CH₂CH₂—C(=CH₂)CH₂CH₂—CH-(COOCH₃)COCH₃ and
(CH₃)₂C=CH—CH₂CH₂—C(CH₃)=CH—CH₂—CH-(COOCH₃)COCH₃
(2.52 g; 0.01 mole) is added.

Sulphuryl chloride (1.34 g; 0.01 mole) is then added at a temperature of −50° C. The mixture is stirred at −50° C. for 30 minutes. After the temperature has been allowed to rise to approximately 20° C. the reaction mixture is poured into water (100 cc) and is then extracted with ethyl ether (3×50 cc). The combined organic phases are dried over magnesium sulphate. After filtration and evaporation of the solvents a yellow oil (4.7 g) is obtained, containing a 55/45 mixture of:
(CH₃)₂C=CH—CH₂CH₂—C(=CH₂)—CH₂CH₂—CCl(COOCH₃)COCH₃ and
(CH₃)₂C=CH—CH₂CH₂—C(CH₃)=CH—CH₂—CCl(COOCH₃)COCH₃.
The yield of isolated product is 65%.

EXAMPLE 11

Methanol (20 cc) and sodium (0.23 g; 0.01 gramme-atom) are introduced, under an argon atmosphere, into a 100 cc round flask. The mixture is cooled to 0° C. and then a 55/45 mixture of:
(CH₃)₂C=CH—CH₂CH₂—C(=CH₂)—CH₂CH₂—CH(COOCH₃)COCH₃ and
(CH₃)₂C=CH—CH₂CH₂—C(CH₃)=CH—CH₂—CH-(COOCH₃)COCH₃

(2.52 g; 0.01 mole) and N-chlorosuccinimide (1.33 g; 0.01 mole) are added. The mixture is stirred at 0° C. for 40 minutes. The reaction mixture is poured into water (100 cc) and then extracted with ether (3×50 cc). The combined organic phases are dried over magnesium sulphate. After filtration and evaporation of the solvent a yellow oil (2.3 g) is obtained which, according to analysis by gas phase chromatography, contains:
6.5% of starting material
41.6% of a 55/45 mixture of:
(CH₃)₂C=CH—CH₂CH₂—C(=CH₂)—CH₂CH₂—CHCl—COOCH₃ and
(CH₃)₂C=CH—CH₂CH₂—C(CH₃)=CH—CH₂—CHCl—COOCH₃
51.8% of a 55/45 mixture of:
(CH₃)₂C=CH—CH₂CH₂—C(=CH₂)—CH₂CH₂—CCl(COOCH₃)COCH₃ and
(CH₃)₂C=CH—CH₂CH₂—C(CH₃)=CH—CH₂—CCl(COOCH₃)COCH₃

EXAMPLE 12

Sodium hydride (0.5 g; 0.01 mole) at a concentration of 50% in mineral oil is introduced, under an argon atmosphere, into a 100 cc round flask. It is washed with dry pentane (3×20 cc). Tetrahydrofuran (20 cc) and a 55/45 mixture of:
(CH₃)₂C=CH—CH₂CH₂—C(=CH₂)—CH₂CH₂—CH(COOCH₃)COCH₃ and
(CH₃)₂C=CH—CH₂CH₂—C(CH₃)=CH—CH₂—CH-(COOCH₃)COCH₃

(2.52 g; 0.01 mole) are then added. The mixture is allowed to react at 25° C. for 5 hours and then a solution of sulphuryl chloride (1.34 g; 0.01 mole) in tetrahydrofuran (10 cc) is added slowly. The mixture is stirred at 25° C. for 3 hours. The reaction mixture is poured into water (100 cc) and then extracted with ethyl ether (3×50 cc). The combined organic phase are dried over magnesium sulphate. After filtration and evaporation of the solvent a yellow oil (3.0 g) is obtained which, according to analysis by gas phase chromatography, contains 62% of a 55/45 mixture of:
(CH₃)₂C=CH—CH₂CH₂—C(=CH₂)—CH₂CH₂—CCl(COOCH₃)COCH₃ and
(CH₃)₂C=CH—CH₂CH₂—C(CH₃)=CH—CH₂—CCl(COOCH₃)COCH₃

According to analysis by gas phase chromatography, the yield is 75%.

EXAMPLE 13

Dry ether (40 cc), sodium (0.236 g; 0.01029 gramme-atom) and a few crystals of ferric chloride are introduced, under an argon atmosphere, into a 100 cc round flask. A 55/45 mixture of:
$(CH_3)_2C=CH—CH_2CH_2—C(=CH_2)—CH_2CH_2—CH(COOCH_3)COCH_3$ and
$(CH_3)_2C=CH—CH_2CH_2—C(CH_3)=CH—CH_2—CH(COOCH_3)COCH_3$
(2.42 g; 0.00961 mole) are then added. The mixture is allowed to react at 25° C. for 4 hours. After cooling to 0° C., a solution of sulphuryl chloride (1.30 g; 0.00963 mole) in ether (5 cc) is added. The mixture is stirred at 0° C. for 30 minutes. The reaction mixture is poured into water (100 cc) and extracted with ethyl ether (3×50 cc). The combined organic phases are dried over magnesium sulphate. After filtration and evaporation of the solvent a yellow oil (2.71 g) consisting of a 55/45 mixture of:
$(CH_3)_2C=CH—CH_2CH_2—C(=CH_2)CH_2CH_2—CCl(COOCH_3)COCH_3$ and
$(CH_3)_2C=CH—CH_2CH_2—C(CH_3)=CH—CH_2—CCl(COOCH_3)COCH_3$
is obtained.

Analysis by gas phase chromatography with an internal standard shows that:
the conversion is 74.8%
the yield of chlorinated products is 67%.

EXAMPLE 14

Dimethylformamide (200 cc), potassium carbonate (16.4 g; 0.118 mole), a 55/45 mixture of:
$(CH_3)_2C=CH—CH_2CH_2—C(=CH_2)—CH_2CH_2—CH(COOCH_3)COCH_3$ and
$(CH_3)_2C=CH—CH_2CH_2—C(CH_3)=CH—CH_2—CH(COOCH_3)COCH_3$
(25.2 g; 0.1 mole) and N-chlorosuccinimide (14 g; 0.104 mole) are introduced, under an argon atmosphere, into a 500 cc round flask. The mixture is allowed to react at 25° C. for 16 hours. The reaction mixture is poured into water (100 cc) and extracted with ethyl ether (3×50 cc). The combined organic phases are dried over magnesium sulphate. After filtration and evaporation of the solvent a slightly yellow oil (27 g) is obtained, which contains 75% of a 55/45 mixture of:
$(CH_3)_2C=CH—CH_2CH_2—C(=CH_2)—CH_2CH_2—CCl(COOCH_3)COCH_3$ and
$(CH_3)_2C=CH—CH_2CH_2—C(CH_3)=CH—CH_2—CCl(COOCH_3)COCH_3$

EXAMPLE 15

Dimethylformamide (150 cc), potassium carbonate (27.6 g; 0.2 mole) and a 55/45 mixture of:
$(CH_3)_2C=CH—CH_2CH_2—C(=CH_2)—CH_2CH_2—CH(COOCH_3)COCH_3$ and
$(CH_3)_2C=CH—CH_2CH_2—C(CH_3)=CH—CH_2—CH(COOCH_3)COCH_3$
(38 g; 0.15 mole) are introduced, under an argon atmosphere, into a 500 cc round flask and then hexachloroethane (42 g; 0.177 mole) is added. The mixture is stirred at 25° C. for 15 hours. Water (200 cc) is added and then the mixture is extracted with ethyl ether (3×50 cc). The combined organic phases are dried over magnesium sulphate. After filtration and evaporation of the solvent an oil (60 g) is obtained which, on being distilled at 150° C. under reduced pressure (1 mm Hg, 0.13 kPa), produces an oil containing 94% of a 55/45 mixture of:
$(CH_3)_2C=CH—CH_2CH_2—C(=CH_2)CH_2CH_2—CCl(COOCH_3)COCH_3$ and
$(CH_3)_2C=CH—CH_2CH_2—C(CH_3)=CH—CH_2—CCl(COOCH_3)COCH_3$
The yield of isolated product is 81%.

The structure of the product obtained is confirmed by the proton nuclear magnetic resonance spectrum.

EXAMPLE 16

Methyl tert-butyl ether (20 cc), potassium carbonate 81.5 g; 0.0108 mole) and a 55/45 mixture of:
$(CH_3)_2C=CH—CH_2CH_2—C(=CH_2)CH_2CH_2—CH(COOCH_3)COCH_3$ and
$(CH_3)_2C=CH—CH_2CH_2—C(CH_3)=CH—CH_2—CH(COOCH_3)COCH_3$
(2.52 g; 0.01 mole) are introduced, under an argon atmosphere, into a 200 cc round flask and then N-chlorosuccinimide (1.33 g; 0.01 mole) is added. The mixture is stirred at 25° C. for 15 hours. Water (100 cc) is added and the mixture is extracted with ethyl ether (3×50 cc). The combined organic phases are dried over magnesium sulphate. After filtration and evaporation of the solvent a colourless oil (2.3 g) is obtained, which contains 91% of a 55/45 mixture of:
$(CH_3)_2C=CH—CH_2Ch_2—C(=CH_2)CH_2CH_2—CCl(COOCH_3)COCH_3$ and $(CH_3)_2C=CH—CH_2CH_2—C(CH_3)=CH—CH_2—CCl(COOCH_3)COCH_3$
The yield of isolated product is 73%.

EXAMPLE 17

N-methylpyrrolidone (20 cc), potassium carbonate (2.8 g; 0.0202 mole) and a 55/45 mixture of:
$CH_2=C(CH_3)—CH_2CH_2—CH(COOCH_3)COCH_3$ and
$(CH_3)_2C=CH—CH_2—CH(COOCH_3)COCH_3$
(3.68 g; 0.02 mole) are introduced, under an argon atmosphere, into a 100 cc round flask and then hexachloroethane (5 g; 0.0211 mole) is added. The mixture is stirred at 25° C. for 15 hours. Water (100 cc) is then added and the mixture is extracted with ethyl ether (3×50 cc). The combined organic phases are dried over magnesium sulphate. After filtration and evaporation of the solvent a slightly yellow oil (6.4 g) is obtained, which contains 16% of starting material and 41% of a 55/45 mixture of:
$(CH_2=C(CH_3)—CH_2CH_2—CCl(COOCH_3)COCH_3$ and
$(CH_3)_2C=CH—CH_2—CCl(COOCH_3)COCH_3$
The yield based on starting material which has reacted is 83%.

EXAMPLE 18

Acetone (80 cc), potassium carbonate (8.28 g; 0.05993 mole), hexachloroethane (13.17 g; 0.05565 mole) and a 55/45 mixture of:
$(CH_3)_2C=CH—CH_2Ch_2—C(=CH_2)—CH_2CH_2—CH(COOCH_3)COCH_3$ and
$(CH_3)_2C=CH—CH_2CH_2—C(CH_3)=Ch—CH_2—CH(COOCH_3)COCH_3$
(10.86 g; 0.04312 mole) are introduced, under an argon atmosphere, into a 250 cc round flask and then stirred for 7 hours at the reflux temperature of the reaction mixture. The reaction mixture is poured into slightly acidified water (100 cc) and then extracted with ethyl ether (3×50 cc). The combined organic phases are dried over magnesium sulphate. After evaporation of the solvent an orangy-yellow liquid (15.45 g) is obtained, which contains a mixture of:
$(CH_3)_2C=CH—CH_2CH_2—C(=CH_2)—CH_2CH_2—CCl(COOCH_3)COCH_3$ and (CH₃)₂C=CH—CH₂CH₂—C(CH₃)=CH—CH₂—CCl(COOCH₃)COCH₃

According to analysis by gas phase chromatography with an internal standard, the yield is 91.5%.

EXAMPLE 19

Dimethylformamide (20 cc), hexachloroethane (2.5 g; 0.0105 mole) and a 55/45 mixture of:
(CH₃)₂C=CH—CH₂CH₂—C(=CH₂)CH₂CH₂CH-(COOCH₃)COCH₃ and
(CH₃)₂C=CH—CH₂CH₂—C(CH₃)=CH—CH₂—CH-(COOCH₃)COCH₃
(2.52 g; 0.01 mole) are introduced, under an argon atmosphere, into a 100 cc round flask and then 1,8-diazabicyclo[5.4.0]undec-7-ene (DBU) (2 g; 0.0131 mole) is added. The mixture is stirred at 25° C. for 4 hours. The reaction mixture is poured into water (100 cc) and then extracted with ethyl ether (3×50 cc). The organic phases are dried over magnesium sulphate. After filtration and evaporation of the solvent a slightly yellow oil (4.12 g) is obtained which, after a flash-distillation, produces a light yellow oil (2.41 g) containing 87% of a 55/45 mixture of:
(CH₃)₂C=CH—CH₂CH₂—C(=CH₂)CH₂CH₂—CCl-(COOCH₃)COCH₃ and
(CH₃)₂C=CH—CH₂CH₂—C(CH₃)=CH₂CH₂—CCl-(COOCH₃)COCH₃

The yield of isolated product is 73%.

EXAMPLE 20

Hexachloroethane (7.11 g; 0.03 mole), tetrabutylammonium hydrogen sulphate (0.342 g; 0.001 mole) and a 55/45 mixture of:
(CH₃)₂C=CH—CH₂—C(=CH₂)—CH₂CH₂—CH-(COCH₃)—COOCH₃ and
(CH₃)₂C=CH—CH₂—C(CH₃)=CH—CH₂—CH-(COCH₃)—COOCH₃
(2.52 g; 0.01 mole) dissolved in methylene chloride (50 cc) are introduced, under an argon atmosphere, into a 100 cc round flask. An aqueous solution (5 cc) containing 50% by weight of sodium hydroxide is then added and the mixture is stirred vigorously at 25° C. for 2 hours. After extraction of the reaction mixture, and chromatography, a 55/45 mixture of:
(CH₃)₂C=CH—CH₂—C(=CH₂)—CH₂CH₂—CCl-(COCH₃)—COOCH₃ and
(CH₃)₂C=CH—CH₂—C(CH₃)=CH—CH₂—CCl-(COCH₃)—COOCH₃
(1.62 g) is obtained.
The yield is 56.5%.

EXAMPLE 21

Hexachloroethane (3.08 g), potassium carbonate (2.07 g) and tetrabutylammonium hydrogen sulphate (0.34 g) in methylene chloride (20 cc) are introduced, under an argon atmosphere, into a 100 cc round flask. A 55/45 mixture of:
(CH₃)₂C=CH—CH₂—C(=CH₂)—CH₂CH₂—CH-(COCH₃)COOCH₃ and
(CH₃)₂C=CH—CH₂—C(CH₃)=CH—CH₂—CH-(COCH₃)COOCH₃
(2.52 g; 10 millimoles) is then added. The reaction mixture is heated under reflux for 5 hours.

A 55/45 mixture of:
(CH₃)₂C=CH—CH₂—C(=CH₂)—CH₂CH₂—CCl-(COCH₃)—COOCH₃ and
(CH₃)₂C=CH—CH₂—C(CH₃)=CH—CH₂—CCl-(COCH₃)—COOCH₃
is obtained with a yield of 20%.

EXAMPLE 22

Potassium carbonate (11.04 g; 0.08 mole), hexachloroethane (4.96 g; 0.021 mole) and acetonitrile (20 cc) are introduced, under an argon atmosphere, into a 100 cc round flask. A 55/45 mixture of:
(CH₃)₂C=CH—CH₂—C(=CH₂)—CH₂CH₂—CH-(COCH₃)—COOCH₃ and
(CH₃)₂C=CH—CH₂—C(CH₃)=CH—CH₂—CH-(COCH₃)COOCH₃
(5.04 g; 0.02 mole) is added.
The reaction mixture is heated under reflux for 3 hours. After cooling, the reaction mixture is poured into water (100 cc) and then extracted with ethyl ether (3×50 cc). The organic phases are washed with water and then dried over magnesium sulphate. After filtration and evaporation of the solvent a 55/45 mixture of:
(CH₃)₂C=CH—CH₂—C(=CH₂)CH₂CH₂—CCl-(COCH₃)—COOCH₃ and
(CH₃)₂C=CH—CH₂—C(CH₃)=CH—CH₂—CCl-(COCH₃)—COOCH₃
is obtained, in the form of an orange oil, with a yield of 95%.

EXAMPLE 23

Hexachloroethane (2.37 g; 0.01 mole), potassium carbonate (1.38 g; 0.01 mole) and nitrobenzene (10 cc) are introduced into a 100 cc round flask. A 55/45 mixture of:
(CH₃)₂C=CH—CH₂—C(=CH₂)—CH₂CH₂—CH-(COCH₃)—COOCH₃ and
(CH₃)₂C=CH—CH₂—C(CH₃)=CH—CH₂—CH-(COCH₃)—COOCH₃
(1.26 g; 0.005 mole) is added.
The heterogeneous mixture is stirred at 110° C. for 5 hours.
After extraction a 55/45 mixture of:
(CH₃)₂C=Ch—CH₂—C(=CH₂)—Ch₂CH₂—CCl-(COCH₃)—COOCH₃ and
(CH₃)₂C=CH—CH₂—C(CH₃)=CH—CH₂—CCl-(COCH₃)—COOCH₃
is obtained with a yield of 78%.

We claim:

1. A process for the preparation of an unsaturated compound α-chlorinated with respect to two electron-attracting groups in a β-position, of the formula:

(Ia)

$$H-\left[\phantom{x}\right]_n\!\!\!-C(X)(Cl)(Y)$$

or (Ib)

$$H-\left[\phantom{x}\right]_n\!\!\!-C(X)(Cl)(Y)$$

in which n denotes an integer from 1 to 10 and X and y, which are identical or different, each denote an electron-attracting group chosen from —CHO, —COR$_1$, —COOR$_2$, —CONR$_3$R$_4$, —CN, —SO$_2$R$_5$ and —NO$_2$, in which R$_1$, R$_2$, R$_3$, R$_4$ and R$_5$ each denote an alkyl radical of 1 to 4 carbon atoms, and R$_5$ may also denote a phenyl radical which is unsubstituted or substituted by methyl, which comprises reacting a halogenating agent selected from the class consisting of sulphuryl chloride, N-chlorosuccinimide, and hexachloroethane with a compound of formula:

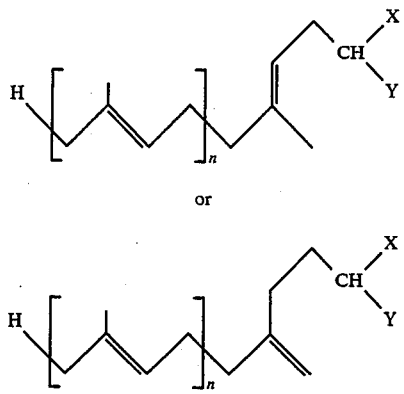

in which n, X and Y are as hereinbefore defined, at a temperature of 0°–120° C. and in the presence of a stoichiometric quantity of a base selected from the group consisting of hydrides, amides, hydroxides and carbonates of alkali and alkaline earth metals, and non-quaternizable amines.

2. A process according to claim 1, in which the reaction is carried out at a temperature below −30° C.

3. A process according to claim 1, in which the base and the halogenating agent are added to the compound of formula (IIa) or (IIb) in solution in an organic solvent.

4. A process according to claim 1, in which the base is added first carried out and then the halogenating agent is added.

5. A process according to claim 1, in which the reaction is carried out in an aliphatic hydrocarbon, aromatic hydrocarbon, ether, ketone, tertiary amide, nitrile, or a nitrated solvent.

6. A process for the preparation of an unsaturated compound α-chlorinated with respect to two electron-attracting groups in a β-position, of the formula:

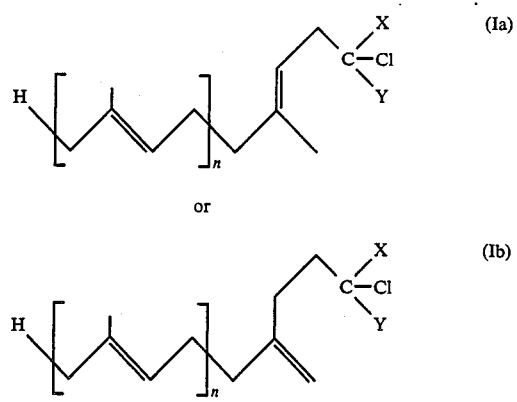

in which n denotes an integer from 1 to 10, and X and Y, which are identical or different, each denote an electron-attracting group chosen from —CHO, —COR$_1$, —COOR$_2$, —CONR$_3$R$_4$, —CN, —SO$_2$R$_5$ and —NO$_2$, in which R$_1$, R$_2$, R$_3$, R$_4$ and R$_5$ each denote an alkyl radical of 1 to 4 carbon atoms, and R$_5$ may also denote a phenyl radical which is unsubstituted or substituted by methyl, which comprises reacting a halogenating agent selected from the class consisting of sulphuryl chloride, N-chlorosuccinimide, and hexachloroethane with a compound of formula:

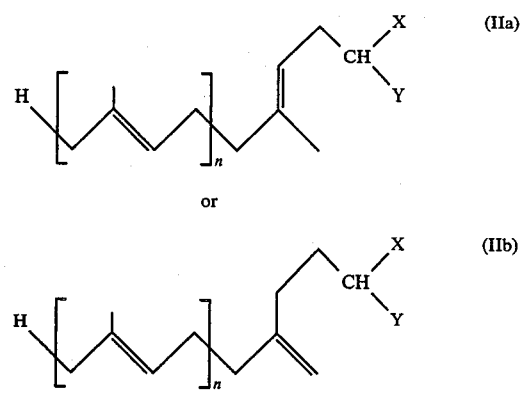

in which n, X and Y are as hereinbefore defined, at a temperature below 0° C. in the presence of a stoichiometric quantity of an alkali metal alcoholate in the corresponding alcohol.

* * * * *